(12) United States Patent
Ma et al.

(10) Patent No.: US 7,149,634 B2
(45) Date of Patent: Dec. 12, 2006

(54) METHOD OF DETERMINING ELASTIC MODULUS

(75) Inventors: Dejun Ma, Hung Hom (CN); Chung-Wo Ong, Hung Hom (CN)

(73) Assignee: The Hong Kong Polytechnic University, Hong Kong (HK)

( * ) Notice: Subject to any disclaimer, the term of this patent is extended or adjusted under 35 U.S.C. 154(b) by 113 days.

(21) Appl. No.: 10/756,298

(22) Filed: Jan. 14, 2004

(65) Prior Publication Data

US 2005/0154540 A1    Jul. 14, 2005

(51) Int. Cl.
*G01L 1/00* (2006.01)
(52) U.S. Cl. ...................................................... 702/41
(58) Field of Classification Search .................. 702/41
See application file for complete search history.

(56) References Cited

U.S. PATENT DOCUMENTS

2003/0060987 A1*    3/2003    Dao et al. ...................... 702/42

OTHER PUBLICATIONS

Yang-Tse Cheng et al., "Relationship Between Hardness, Elastic Modulus, and the Work of Indentation", Applied Physics Letters, 1998, pp. 614-616, vol. 73, No. 5, American Institute of Physics, USA.

W.C. Oliver et al., "An Improved Technique for Determining Hardness and Elastic Modulus Using Load and Displacement Sensing Indentation Experiments", J. Mater. Res., 1992, pp. 1564-1583, vol. 7, No. 6, Materials Research Society, USA.

M.Dao et al., "Computational Modeling of the Forward and Reverse Problems in Instrumented Sharp Indentation", Acta Materialia Inc., 2001, pp. 3899-3918, vol. 49, Elsevier Science Ltd., England.

* cited by examiner

*Primary Examiner*—John Barlow
*Assistant Examiner*—Cindy Khuu
(74) *Attorney, Agent, or Firm*—Buchanan Ingersoll & Rooney PC

(57) ABSTRACT

A method and apparatus of determining an elastic modulus of a material having a Poisson's ratio v by a Berkovich indenter having an elastic modulus E; a Poisson's ratio v, and a cross sectional area A(h) as a function of depth are provided. The method and apparatus model the Berkovich indenter with a conical shape and a spherical cap.

18 Claims, 15 Drawing Sheets

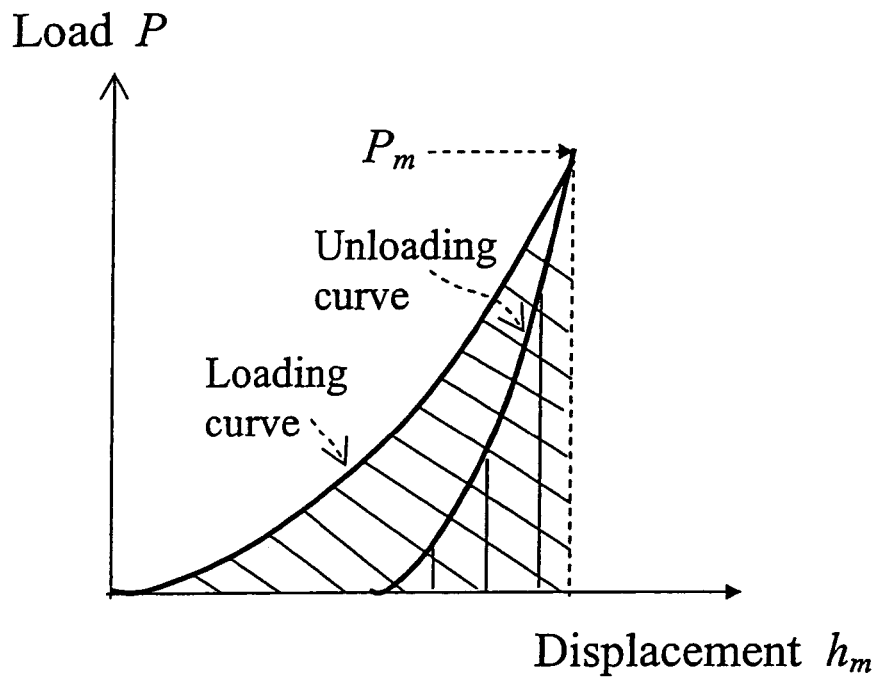
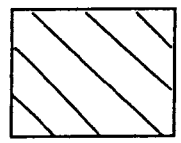    $W$ : Total work = Area under the loading curve
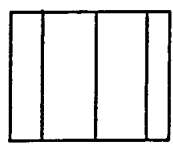    $W_e$ : Elastic work = Area under the unloading curve
Figure 3
PRIOR ART

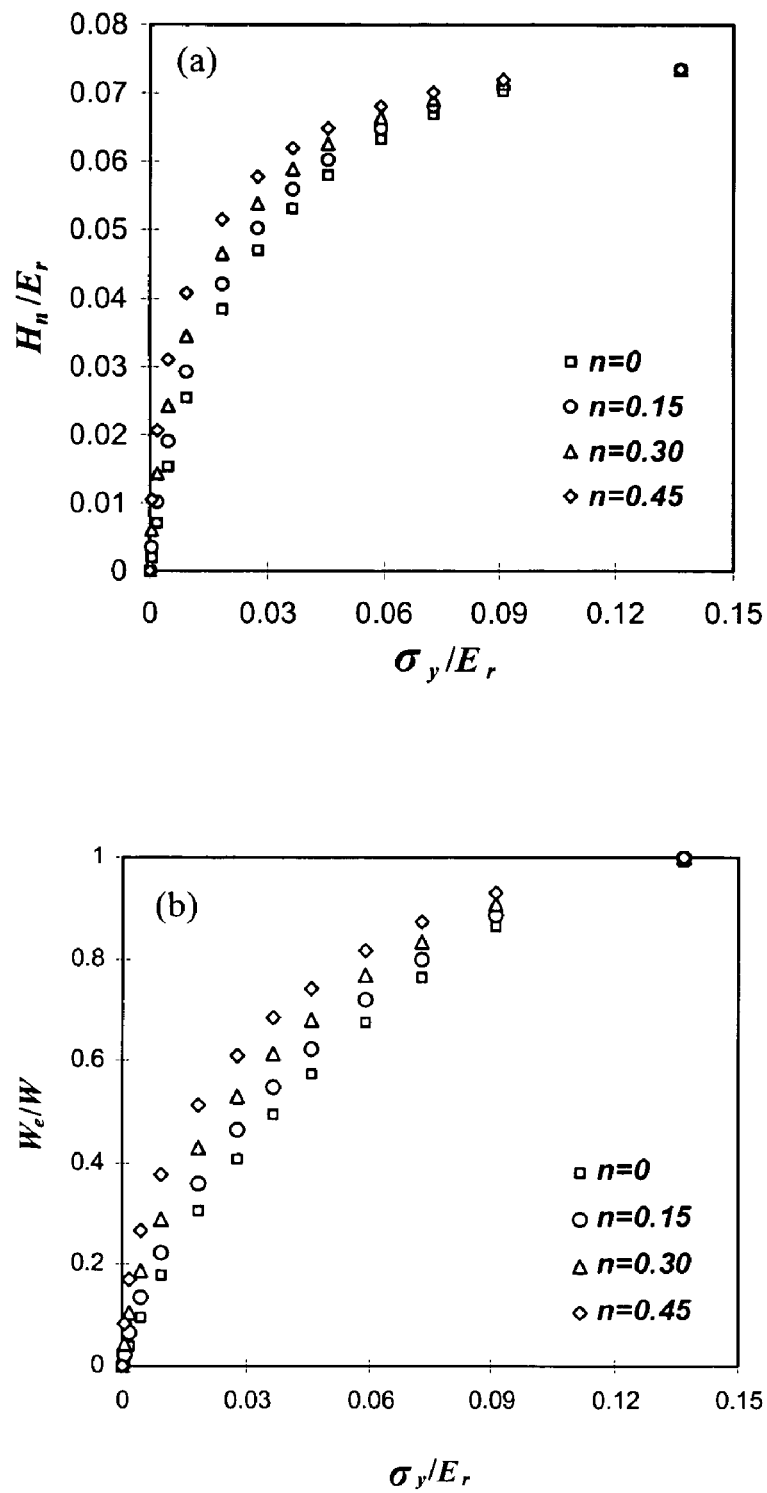
Figure 5 (a) and (b)

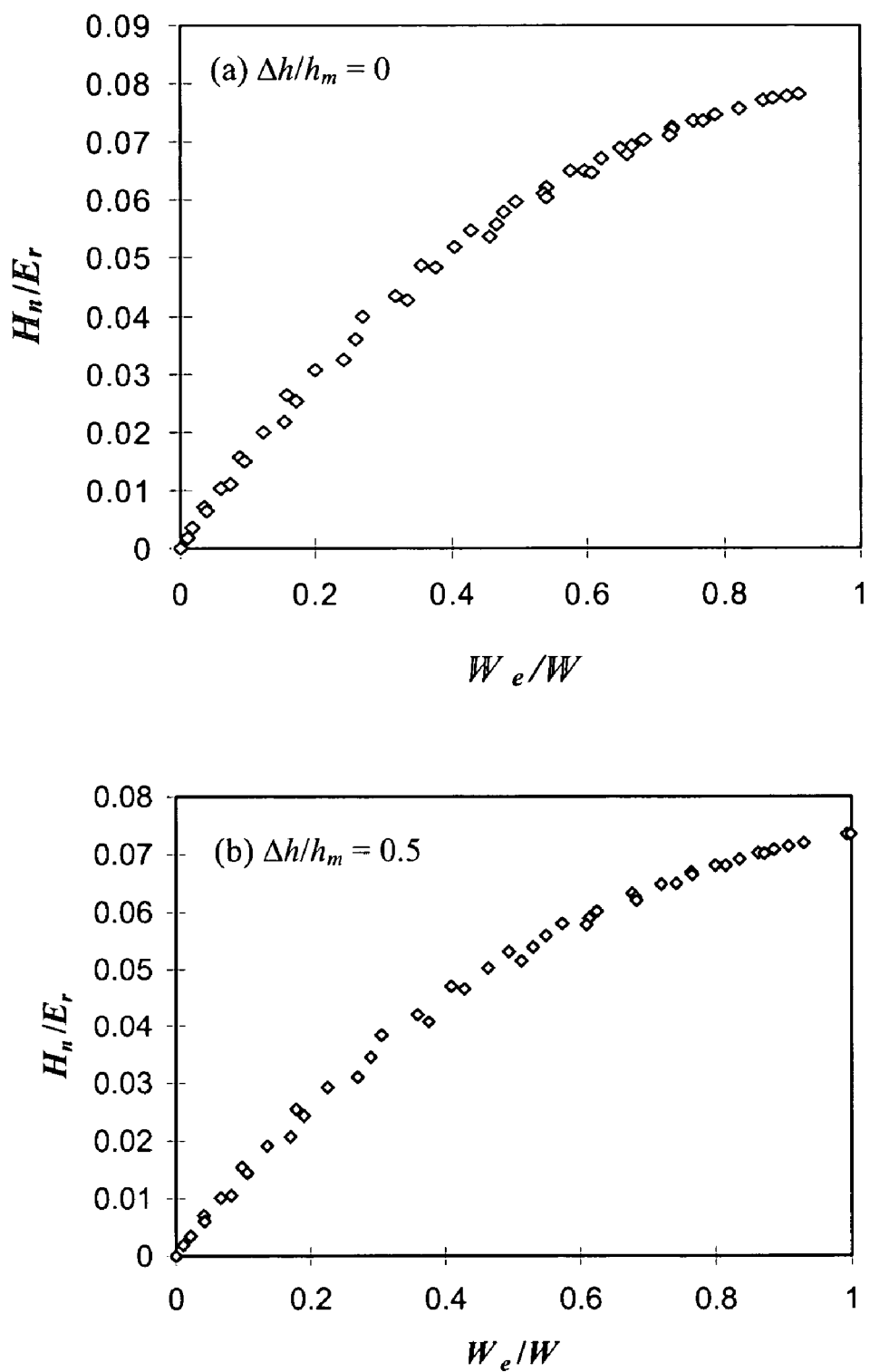
Figure 6 (a) and (b)

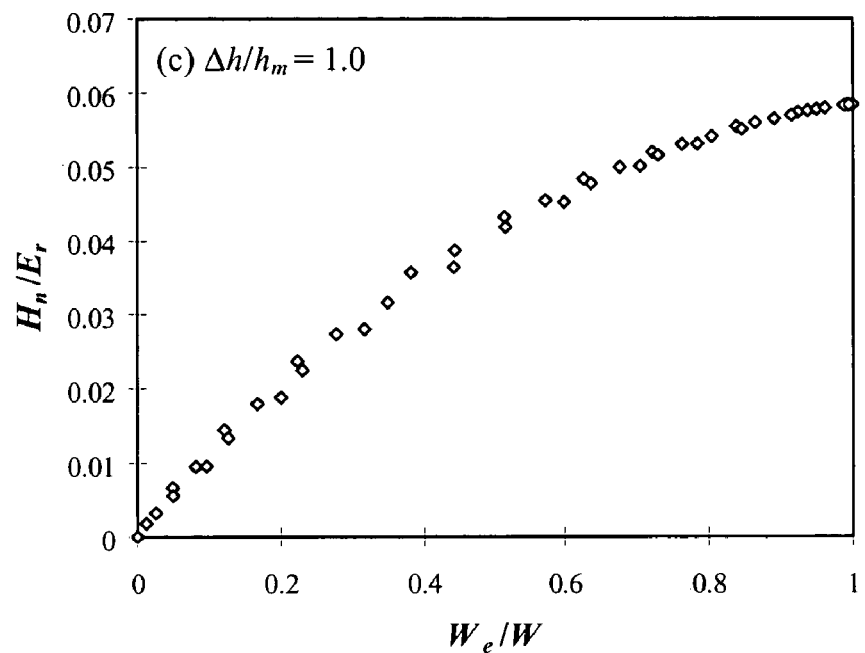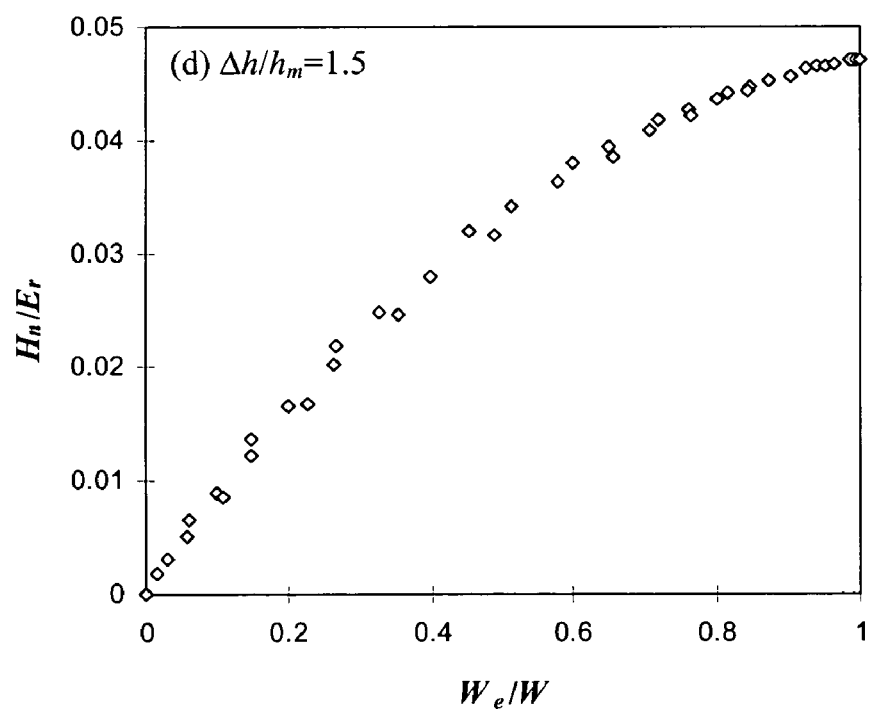
Figure 6 (c) and (d)

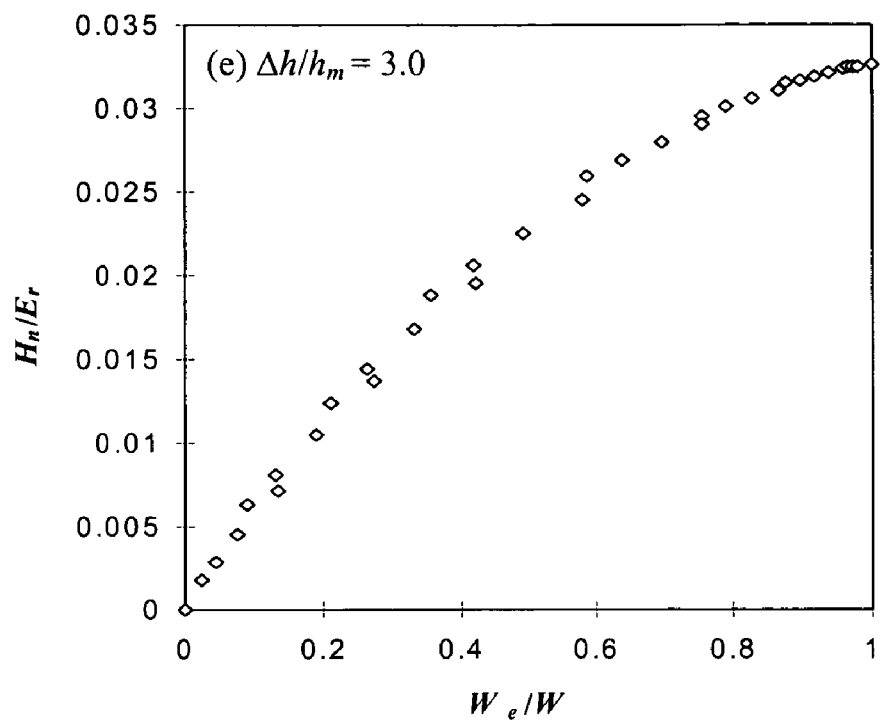
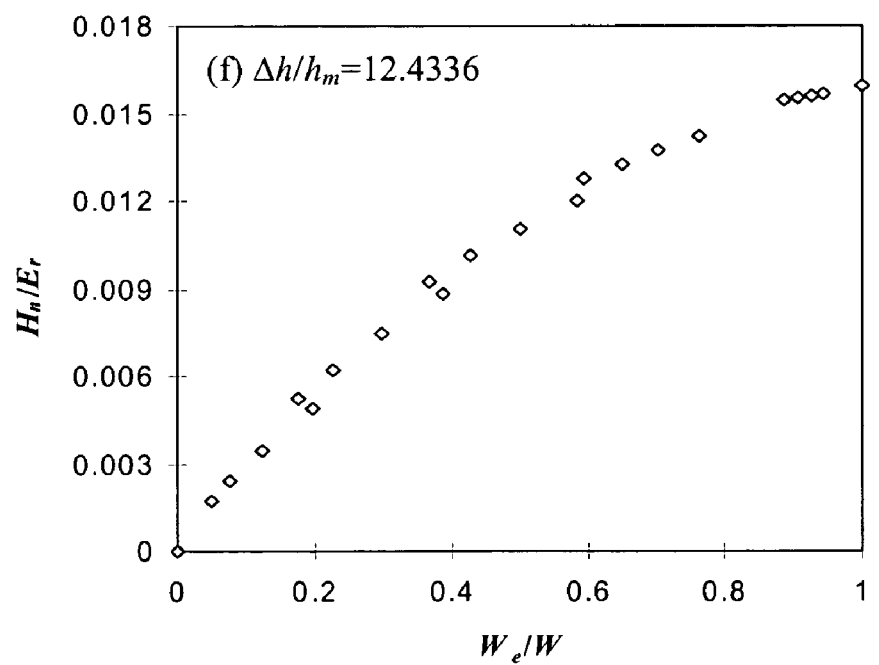
Figure 6 (e) and (f)

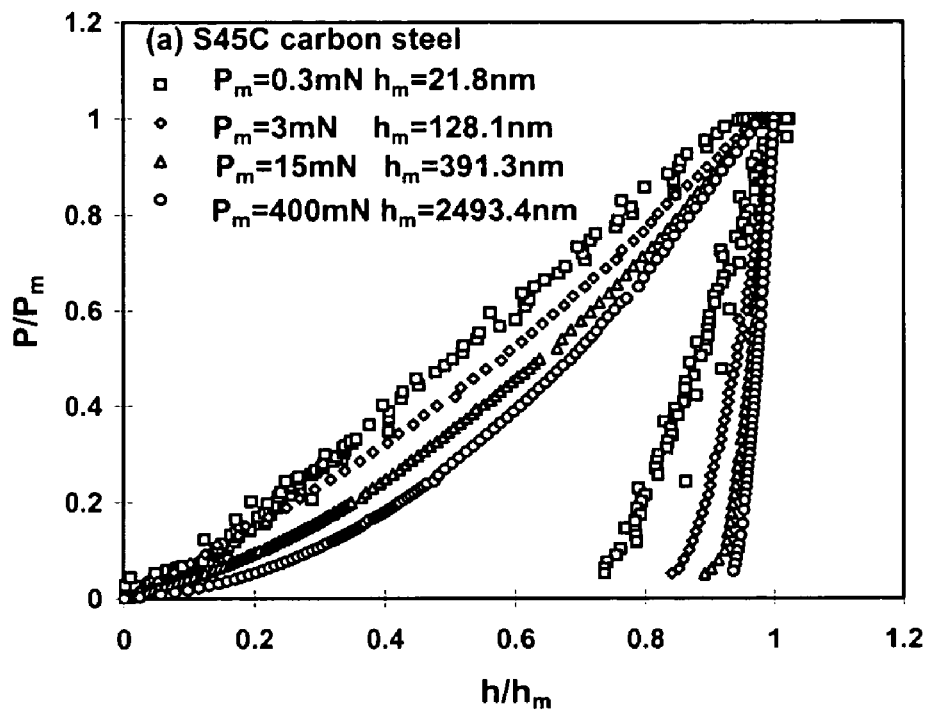
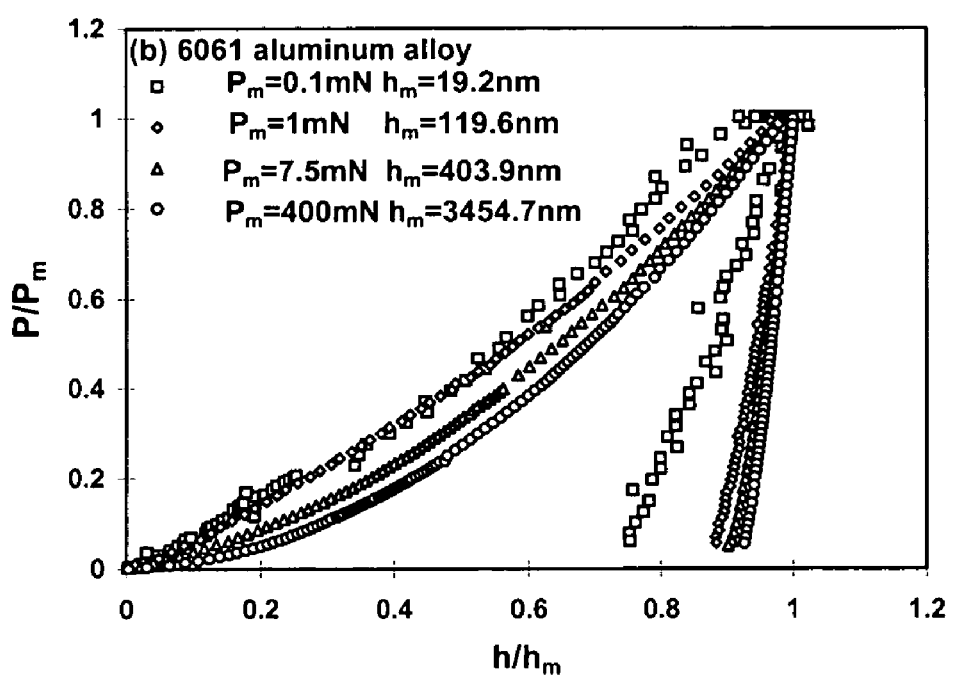
Figure 8 (a) and (b)

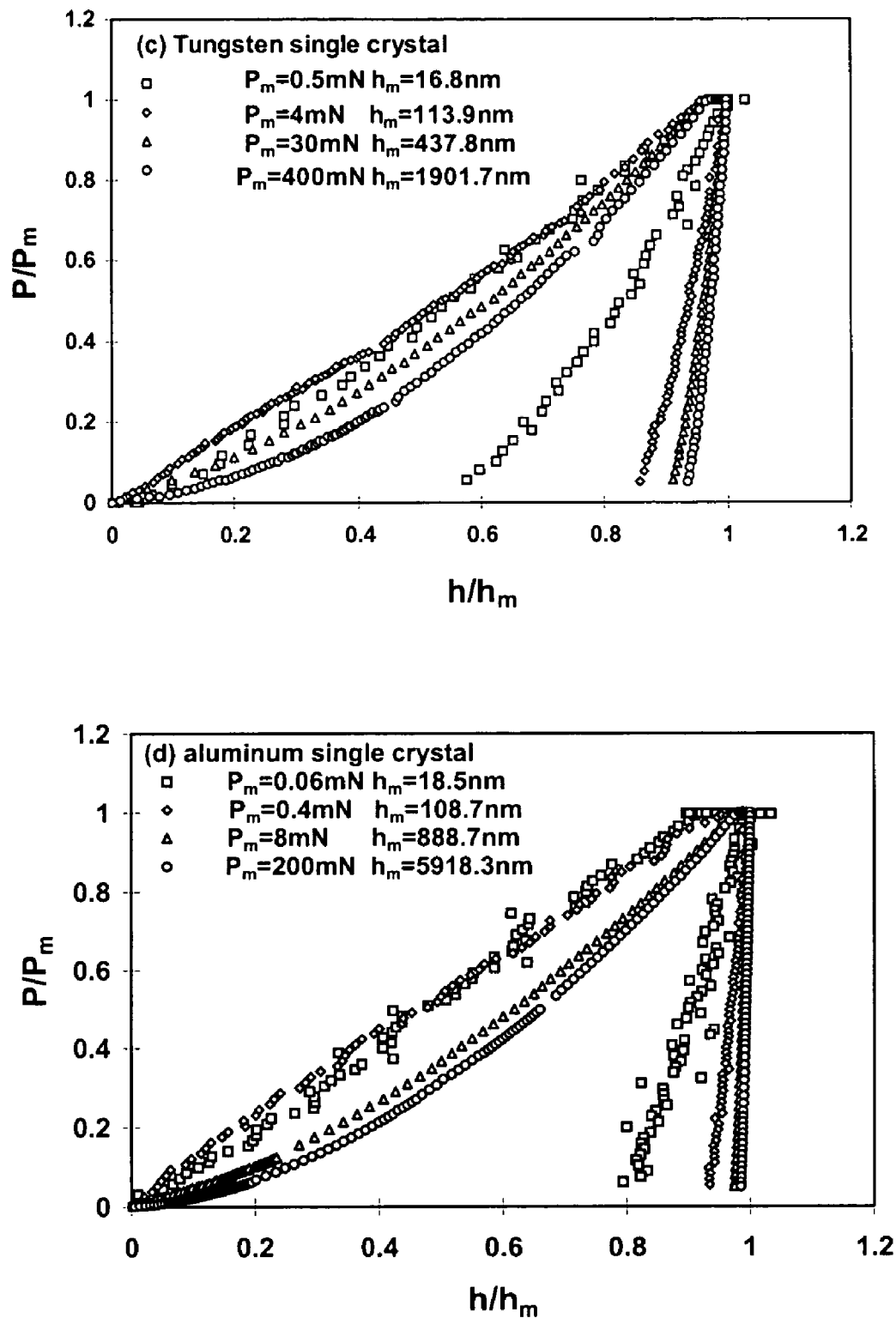
Figure 8 (c) and (d)

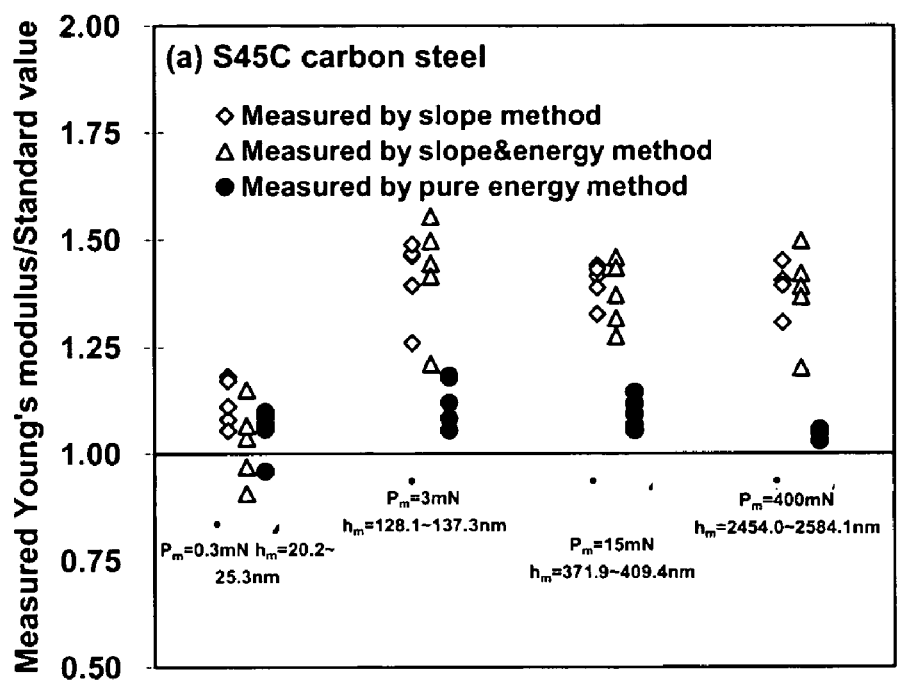
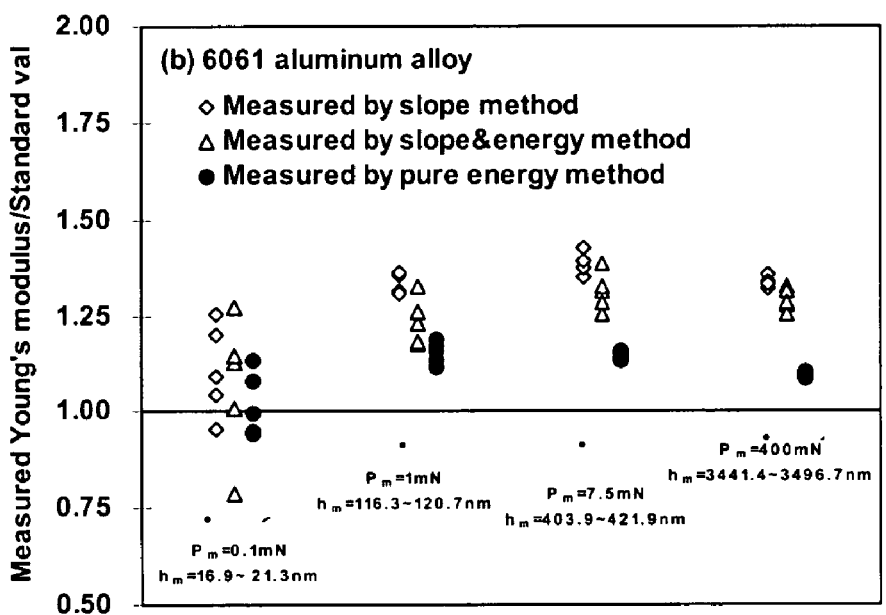
Figure 9 (a) and (b)

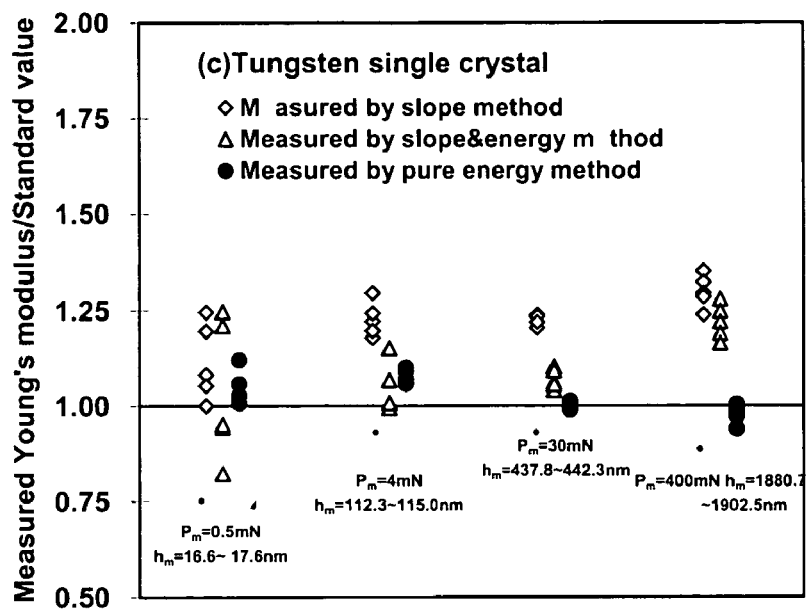
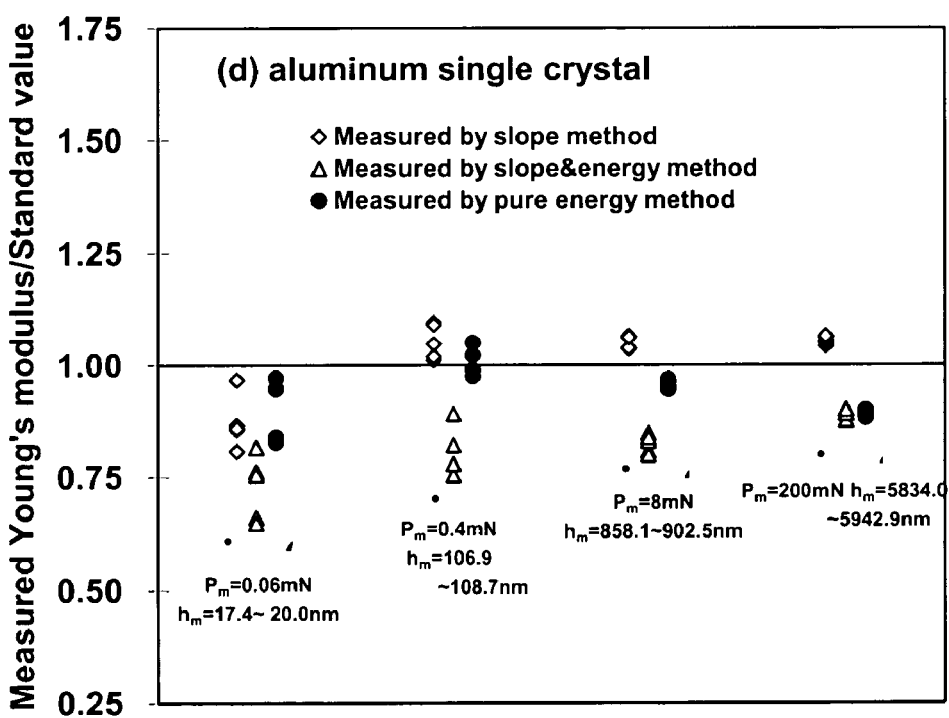
Figure 9 (c) and (d)

METHOD OF DETERMINING ELASTIC MODULUS

FIELD OF THE INVENTION

This invention relates to a method for determining elastic modulus, particularly by indentation techniques.

BACKGROUND OF THE INVENTION

Elastic modulus plays a central role in the understanding of the mechanical behavior of a material. In practice, there is a need to determine the elastic modulus of materials on small scales. In the past decade, depth-sensing indentation technique has become a very useful tool for this purpose, particularly in determining the mechanical properties of materials on small scales by recording the load v.s. displacement of the indenter during indentation (loading and unloading curves), from which the mechanical properties of the indented material are estimated.

Oliver and Pharr (*J. Mater. Res.* 7, 1564, (1992)) proposed a classic formula correlating the reduced elastic modulus ($E_r$), the initial slope of the unloading curve $S_u$, and the projected contact area $A(h_c)$ at the maximum indentation load:

$$E_r = \frac{\pi}{2\beta}\left(\frac{S_u}{\sqrt{A(h_c)}}\right) \quad (1)$$

$A(h_c)$ is the cross sectional area of the indenter corresponding to the contact depth $h_c$ at the maximum indentation load, as shown in FIG. 1. $E_r$ is defined by the expression $$\frac{1}{E_r} = \frac{1-v^2}{E} + \frac{1-v_i^2}{E_i}$$

with E and v being the elastic modulus and Poisson's ratio of indented material, and $E_i$ and $v_i$ being those of the indenter. β is an indenter shape dependent constant. In this method, $A(h_c)$ is estimated indirectly from the unloading curve in order to avoid direct imaging of the impression. As such, errors could be introduced, especially when "piling-up" of the indented material at the point of contact occurs. This situation of "piling-up" is shown in FIG. 2. Moreover, the initial unloading slope $S_u$ of the unloading curve is needed, but it is sometimes difficult to be determined accurately, especially in the cases where the signal-to-noise ratio is low. Because this method requires the use of $S_u$, it is therefore referred as the slope method in the context.

Regarding the above deficiencies, in recent years, some researchers sought for alternative approaches, such as examining the relationship between hardness, elastic modulus and indentation work on the basis of numerical simulation for ideally sharp indentation. It was found (Y.-T. Cheng and C.-M. Cheng, *Appl. Phys. Lett.* 73, 614(1998)) that the ratio of hardness (H) to reduced elastic modulus can be related to the ratio of elastic work ($W_e$) to total work (W) in an indentation, in implicit form:

$$H/E_r = f(W_e/W) \quad (2)$$

where $H = P_m/A(h_c)$ is measured at the maximum indentation load $P_m$; $A(h_c)$ is the projected contact area corresponding to the contact depth $h_c$, as shown in FIG. 1; $W_e$ and W are the work done by the indenter in the unloading and the loading processes, respectively, as shown in FIG. 3. By combining Eq(1) and Eq(2), $E_r$ can be determined as:

$$E_r = [\pi/(2\beta)^2] f(W_e/W)[S_u^2/P_m] \quad (3)$$

Compared with the slope method, this method does not require $A(h_c)$, but it still relies on the use of the initial unloading slope, which may be the major source of error. Associated with these particular features, this approach is denoted as the slope&energy method in the context. Further, in Cheng et. al. paper, the indenter is assumed to be ideally sharp, so that the treatment is not detailed enough for the model to be practically useful, but more work has to be done to take the indenter bluntness effects into consideration.

OBJECTS OF THE INVENTION

Therefore, it is an object of this invention to reduce at least one or more of the problems as set forth in the prior art. As a minimum, it is an object of this invention to provide the public with a useful choice.

SUMMARY OF THE INVENTION

Accordingly, the invention provides a method of determining the elastic modulus of a material having a Poisson's ratio v, by using a Berkovich indenter having an elastic modulus $E_i$, a Poisson's ratio $v_i$, and a cross sectional area A(h) as a function of depth h, wherein the Berkovich indenter is modeled with a conical shape having a spherical cap. The modeling conical shape is assigned to have a half-included θ, and a radius R of the spherical cap or an absolute bluntness value Δh to ensure that its cross sectional area is the same as A(h) for all h values. Δh is related to R by the formula Δh=(1/sin θ−1)R. The maximum indentation load $P_m$, the maximum indentation depth $h_m$, the elastic work $W_e$ done during unloading, and the total work W done during loading are measured. A nominal hardness defined as $$H_n \equiv \frac{P_m}{A(h_m)}$$

is then determined. A set of estimates of $$\frac{H_n}{E_r}$$

is obtained from a set of relationships correlating $$\frac{H_n}{E_r} \text{ and } \frac{W_e}{W}$$

derived from numerical simulations of the indentation processes corresponding to different settings of relative bluntness defined as $\Delta h/h_m$, wherein $E_r$ is the reduced elastic modulus of the indented material defined by the formula $$\frac{1}{E_r} = \frac{1-v^2}{E} + \frac{1-v_i^2}{E_i}.$$

Then an estimate of $$\frac{H_n}{E_r}$$

corresponding to the measured $\Delta h/h_m$ value is obtained through interpolation. The value of $E_r$ is calculated by dividing the measured $H_n$ with the estimated $$\frac{H_n}{E_r}$$

value. The elastic modulus of the indented material E is then obtained from the formula $$E = \frac{1-v^2}{\frac{1}{E_r} - \frac{1-v_i^2}{E_i}}.$$

Preferably, the relationship between $$\frac{H_n}{E_r} \text{ and } \frac{W_e}{W}$$

may be described as $$\left(\frac{H_n}{E_r}\right)_j = \sum_{i=1}^{6} a_{ij}\left(\frac{W_e}{W}\right)^i,$$

where the values of the coefficients $a_{ij}$ depend on the area function A(h) of the indenter at large h beyond the blunt region.

Preferably, i is from one to six to index the six terms in a relationship between $$\frac{H_n}{E_r}$$

and $$\frac{W_e}{W}.$$

Preferably, j is from one to six corresponding to six $$\frac{H_n}{E_r} - \frac{W_e}{W}$$

relationships obtained from six different settings of relative bluntness $\Delta h/h_m$.

This invention also provides an apparatus for determining an elastic modulus E of a material having a Poisson's ratio v by using a Berkovich indenter which has an elastic modulus $E_i$, a Poisson's ratio $v_i$, a cross sectional area A(h) as a function of depth h, and is modeled with a blunt conical shape having the same A(h) at all h values. The invention includes a processor incorporating the above methods.

It is another aspect of this invention to provide a method of determining an elastic modulus of a material upon indentation by a Berkovich indenter including the steps of:

a) measuring maximum load $P_m$, indentation depth, elastic work and total work;

b) determining a nominal hardness value calculated from the measured maximum load and indentation depth;

c) utilizing a set of material independent correlations between the ratio of nominal hardness to reduced modulus, and the ratio of elastic work to total work to calculate said elastic modulus.

BRIEF DESCRIPTION OF THE DRAWINGS

Preferred embodiments of the present invention will now be explained by way of example and with reference to the accompanying drawings in which:

FIG. 3 shows the total work W and elastic recovery work $W_e$ in the loading and unloading processes;

FIG. 5 shows the functional dependence of (a) $H_n/E_r$ and (b) $W_e/W$ on $\sigma_y/E_r$ and n, for a relative indenter bluntness $\Delta h/h_m=0.5$;

FIG. 6 shows the function-like relationships between $H_n/E_r$ and $W_e/W$ for relative indenter bluntness $\Delta h/h_m$ equal to (a) 0, (b) 0.5, (c) 1.0, (d) 1.5, (e) 3.0 and (f) 12.4336;

DETAILED DESCRIPTION OF THE PREFERRED EMBODIMENT

This invention is now described by way of example with reference to the figures in the following paragraphs. List 1 is a list showing the mathematical symbols used in this specification so that the symbols may be easily referred to.

Objects, features, and aspects of the present invention are disclosed in or are obvious from the following description. It is to be understood by one of ordinary skill in the art that the present discussion is a description of exemplary embodiments only, and is not intended as limiting the broader aspects of the present invention, which broader aspects are embodied in the exemplary constructions.

The invented method does not involve the use of contact area $A(h_c)$ and the slope of initial unloading $S_u$, and hence may be referred as the pure energy method in the context.

Figure 4:
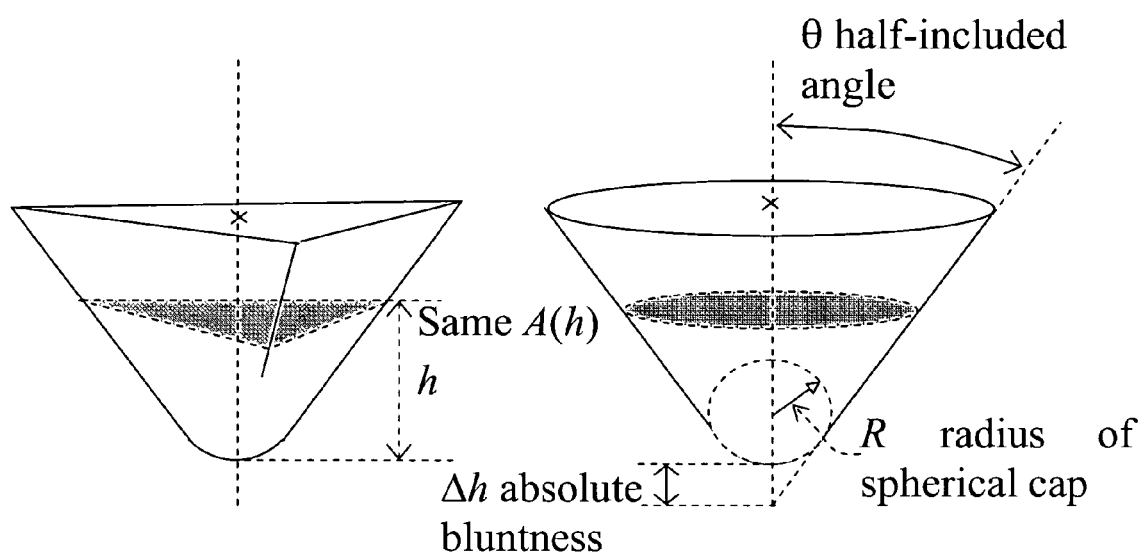
FIG. 4 shows the equivalence between a real Berkovich indenter and a non-ideal conical indenter model based on the same-depth-same-area principle.

A Berkovich indenter is used in this exemplary embodiment, considering that it is the most popular type of indenter used for indentation tests. Importantly, the indenter is assumed to have some degree of bluntness, referring to the fact that a real indenter can never be ideally sharp due to the truncation caused in the fabrication process. The area function $A(h)$, i.e. the cross sectional area of the indenter at any depth h from its apex, is attained according to the standard tip calibration procedures proposed by Oliver and Pharr (J. Mater. Res. 7, 1564 (1992)). For a real Berkovich indenter, the area function can be described by a formula $A(h)=24.5 h^2+c_1 h+c_2 h^{1/2}+c_3 h^{1/4}+c_4 h^{1/8}+c_5 h^{1/16}+c_6 h^{1/32}+c_7 h^{1/64}+c_8 h^{1/128}$, where $c_1, c_2, \ldots,$ and $c_8$ are coefficients depending on the bluntness. The real Berkovich indenter is modeled with a conical indenter shape having a half-included angle $\theta$, and a spherical cap of a radius R (or equivalently an absolute bluntness $\Delta h$) as depicted in FIG. 4. This conical model is established according to the assumption that its cross sectional area at any h is equal to $A(h)$ of the real indenter. At large h beyond the blunt region, $A(h)$ approaches to $24.5 h^2$ of an ideal Berkovich indenter, and so $\theta$ is calculated to be $\tan^{-1} (24.5/\pi)^{1/2}=70.3$ degree. By least square fit to the area function $A(h)$ of the real indenter, R is then determined, and $\Delta h$ is equal to $(1/\sin \theta - 1)R$. Furthermore, a quantity, relative bluntness, is defined as $r_b=\Delta h/h_m$. The elastic modulus $E_i$ and Poisson's ratio $v_i$ of the indenter material are known as the indenter shall be made of materials with known properties.

It should be emphasized that any sharp indenter with some degree of bluntness can be used in the invented method. This includes all blunt conical indenters and blunt pyramidal indenters. For instance, a 3-sided indenter with its faces having an inclination angle different from that of a standard Berkovich indenter, or a 4-sided Vickers indenter can be used. These indenter shapes are all able to be modeled with an equivalent conical shape having an half-included angle $\theta$ and a spherical cap, where the value of $\theta$ is determined according to the cross sectional area of the real indenter at large h beyond the blunt region.

The indented material is assumed to:

1. behave as an isotropic and rate-independent solid;

2. obeys the Von Mises yield criterion and pure isotropic hardening rule and 3. respond within the framework of continuum mechanics.

The uniaxial stress-strain relations take the form of linear elasticity combined with the Hollomon's power law hardening, which can be expressed as:

$$\sigma = \begin{cases} E\varepsilon & \varepsilon \leq \varepsilon_y \\ \sigma_y(\varepsilon/\varepsilon_y)^n & \varepsilon > \varepsilon_y \end{cases} \quad (4)$$

where E is the elastic modulus, $\sigma$ and $\epsilon$ are the true stress and true strain, $\sigma_y$ and $\epsilon_y=\sigma_y/E$ are the yield stress and yield strain, and n is the strain hardening exponent. The indenter is assumed to deform elastically during indentation. The contact interface between the indenter and the indented material is assumed to be free of friction.

Figure 1:
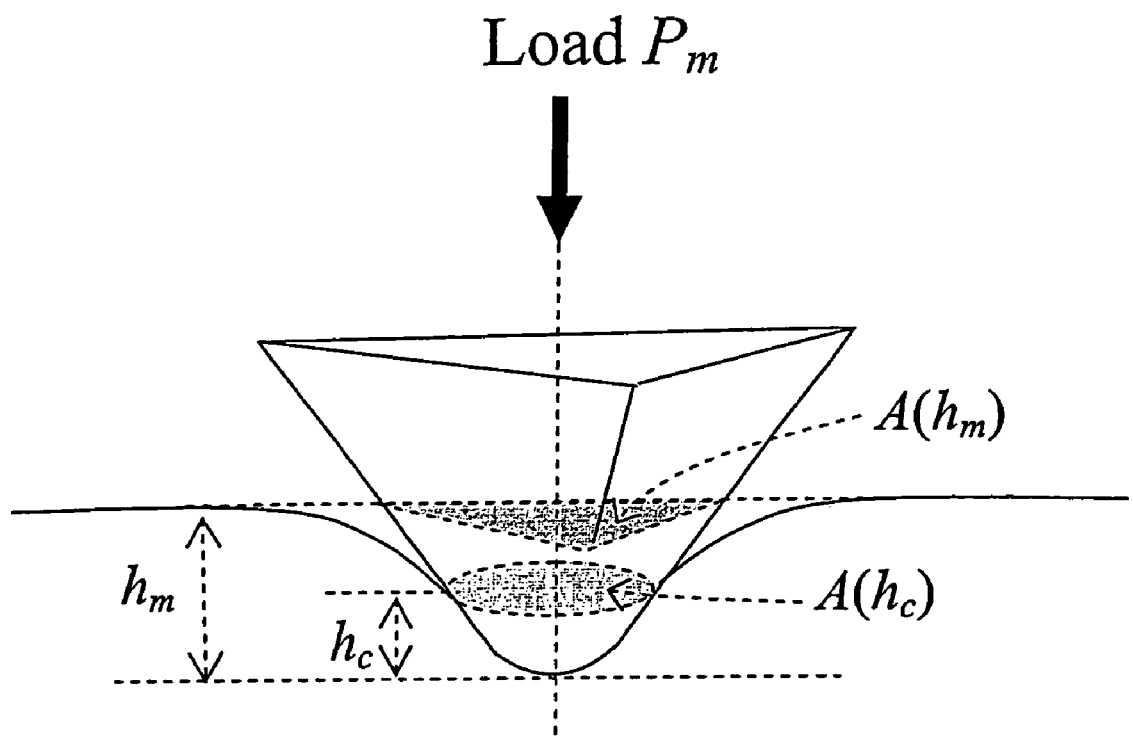
FIG. 1 shows the areas $A(h_c)$ and $A(h_m)$ used to define hardness $H=P_m/A(h_c)$ and nominal hardness $H_n=P_m/A(h_m)$.
Figure 2:
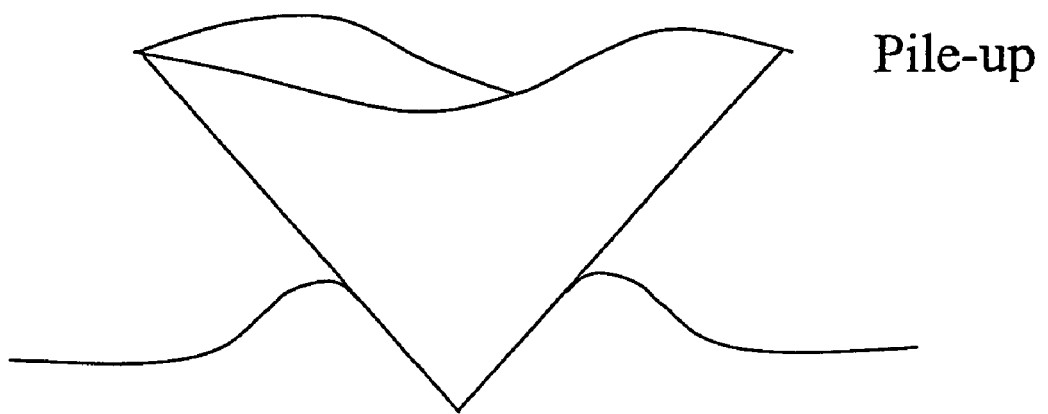
FIG. 2 shows the situation where the indented surface "pile-up" during indentation.

A nominal hardness $H_n$ defined as $P_m/A(h_m)$ is used as an important parameter in this invention, which is different from the conventional hardness $H=P_m/A(h_c)$. They are physically different because the denominator of the former is $A(h_m)$ which is the projected area corresponding to the maximum displacement $h_m$, whereas that of latter is the projected contact area $A(h_c)$ corresponding to the contact depth $h_c$. The difference between $A(h_m)$ and $A(h_c)$ is shown in FIG. 1. The reason for using $H_n$ is that both $P_m$ and $h_m$ can be easily directly measured with high accuracy.

The two quantities, that is, nominal hardness $H_n=P_m/A(h_m)$ and work ratio $W_e/W$ are treated to be the indentation responses, and should be functions of the elastoplastic properties (E, v, $\sigma_y$, n) of the tested material, the elastic modulus ($E_i$), Poisson's ratio ($v_i$) and absolute bluntness ($\Delta h$) of the indenter and the indentation depth ($h_m$). Under this situation, $H_n$ and $W_e/W$ can be described implicitly as:

$$H_n=f_H(E, v, \sigma_y, n, E_i, v_i, \Delta h, h_m) \quad (5)$$

$$W_e/W=f_W(E, v, \sigma_y, n, E_i, v_i, \Delta h, h_m) \quad (6)$$

Like Dao's analysis for sharp indentation, these two functions may be further simplified by introducing a reduced elastic modulus $E_r$ to combine the overall elasticity effects from the indenter and indented material, so that:

$$H_n=f_H(\sigma_y, n, E_r, \Delta h, h_m) \quad (7)$$

$$W_e/W=f_W(\sigma_y, n, E_r, \Delta h, h_m) \quad (8)$$

Applying $\Pi$ theorem of dimensional analysis, functions (7) and (8) can be rewritten in the following dimensionless forms:

$$H_n/E_r=\Phi_H(\sigma_y/E_r, n, \Delta h/h_m) \quad (9)$$

$$W_e/W=\Phi W(\sigma_y/E_r, n, \Delta h/h_m) \quad (10)$$

To investigate the relationship between $H_n/E_r$ and $W_e/W$, the explicit solutions of the two functions (9) and (10) are needed. To achieve the solutions, numerical analysis is required.

Finite element analyses (FEA) were carried out to simulate indentation processes with a non-ideal conical indenter model to derive the explicit forms of functions (9) and (10). Referring to the implicit function forms of (9) and (10), they depend on three parameters, i.e. $\sigma_y/E_r$, n and $\Delta h/h_m$. For the first one, $E_r$ merges the elasticity effects of the indented material and the indenter material ($E_i$, $v_i$, E, and v). If the indenter is assumed to be rigid, and $E_r$ is assigned with a fixed number, $\sigma_y/E_r$ can be varied by varying $\sigma_y$ alone. For the third parameter $\Delta h/h_m$, if $h_m$ is assigned with a fixed value, it can be varied by varying $\Delta h$ alone.

Based on all the above considerations, only the four property parameters ($\sigma_y$, n, E and v) of the indented material, the absolute bluntness ($\Delta h$) of indenter tip and the maximum indentation depth ($h_m$) are needed to be assigned with some values or ranges of values in the numerical analysis. They are $\sigma_y=35\sim21000$ MPa, $n=0\sim0.45$, $E=70$ GPa, $v=0.3$, $\Delta h=0\sim12.4336$ μm and $h_m=1$ μm.

The indentation responses corresponding to different relative bluntnesses $\Delta h/h_m=0, 0.5, 1.0, 1.5, 3.0$ and $12.4336$ were investigated. Of course, more than six values of relative bluntnesses $\Delta h/h_m$ may be used, which may have values different from the above. However, later results showed that the above settings of $\Delta h/h_m$ values may be sufficient. In particular, high $\Delta h/h_m$ values correspond to indentation depths comparable with the indenter bluntness. On the contrary, low $\Delta h/h_m$ values correspond to deep indentations where the indenter behaves as if an ideal one. FIG. 5(a) and (b) show the functional dependence of $H_n/E_r$ and $W_e/W$ on $\sigma_y/E_r$ and n, corresponding to a relative bluntness $\Delta h/h_m=0.5$.

For any one of the above settings of $\Delta h/h_m$, the data of $H_n/E_r$ and $W_e/W$ calculated for different combinations of $\sigma_y''/E_r$ and n are found to have a nearly one-to-one function-like correspondence. The six function-like relationships between $H_n/E_r$ and $W_e/W$ corresponding to the six $\Delta h/h_m$ settings specified above are plotted in FIG. 6 (a)–(f). Each of them is expressed with a six-term polynomial in the form of:

$$\left(\frac{H_n}{E_r}\right)_j = \sum_{i=1}^{6} a_{ij} \left(\frac{W_e}{W}\right)^i \quad (11)$$

where $a_{ij}$'s (i, j=1, 2, ..., and 6) are the fitting coefficients attained from least square fits to reproduce the correlation between $H_n/E_r$ and $W_e/W$ values. The subscript i is used to index the terms in a polynomial. The subscript j is used to specify a function corresponding to a certain $\Delta h/h_m$. The values of $a_{ij}$'s depend on the cross sectional area of the indenter beyond the blunt region. The cross sectional area of the indenter beyond the blunt region affects the half-included angle $\theta$ of the conical indenter model used in the analyses, and affects the mechanical response of the indented material and hence the values of the $a_{ij}$ coefficients. For a Berkovich indenter, the area function at large h is $A(h)=24.5\ h^2$. This gives a $\theta$ of 70.3 degree, and the $a_{ij}$ coefficients derived are shown in Table I. It is further noted that the absolute bluntness $\Delta h$ of an indenter does not affect the values of the $a_{ij}$ coefficients.

It should be noted that the use of six fitting coefficients $a_{ij}$ for each function-like relationship is not a must for this invention to work. Less than six fitting coefficients may be used but this may reduce the accuracy of the correlations between $H_n/E_r$ and $W_e/W$. More than six fitting coefficients may be used but this may not enhance the accuracy significantly. Moreover, the use of six $\Delta h/h_m$ is also not a must, but may already be adequate for giving an accurate estimate of the elastic modulus of the indented material.

Importantly, the above correlations between $H_n/E_r$ and $W_e/W$ are found to be universal to all materials, as long as the indented materials and indenters fulfill the above requirements and/or assumptions. Such a finding may simplify significantly the whole process for determining elastic modulus. Only four values, i.e. $P_m$ and $h_m$ (to obtain $H_n$), and $W_e$ and W are required to be measured, which can be done relatively easily with high accuracy. The experimentally measured value of the relative bluntness $\Delta h/h_m$ is usually not equal to any one of the six $\Delta h/h_m$ values specified above. Therefore, a set of estimates of $H_n/E_r$ corresponding to the six $\Delta h/h_m$ values are derived first, from which an estimate of $H_n/E_r$ corresponding to the measured $\Delta h/h_m$ value is obtained through interpolation. From the result, $E_r$ is calculated by dividing $H_n$ with the estimated $H_n/E_r$ value. The elastic modulus E of the indented material may then be found from $$\frac{1}{E_r} = \frac{1-v^2}{E} + \frac{1-v_i^2}{E_i}.$$

At the very least, one of the major sources of error in the current methods, the initial unloading slope, may no longer be required to determine the elastic modulus according to this invention. Further, this invention has already considered the fact that a Berkovich indenter tip is not ideally sharp.

The area function of an indenter would change all the time with increasing duration of use, due to wear and tear of the indenter material. The change in the absolute bluntness $\Delta h$ would of course give rise to erroneous evaluation of relative bluntness $\Delta h/h_m$, which eventually results in a wrong estimate of $E_r$. If this happens, the area function should be recalibrated. However, this process may not have to be done too often, possibly once per year, because the rate of wear of an indenter made of a hard material such as diamond is slow.

It may be desirable to obtain different sets of $P_m$ and $h_m$ (to obtain $H_n$), $W_e$ and W by repeated experiments to obtain an average value of E to further enhance accuracy.

With the data in Table I, a program incorporating the method of this invention may be written. Such a program may then be incorporated into existing machines for measuring elastic modulus, which are generally capable of measuring maximum load $P_m$, the maximum indentation depth $h_m$, elastic work $W_e$, and total work W, to determine the elastic modulus of various materials.

Figure 7:
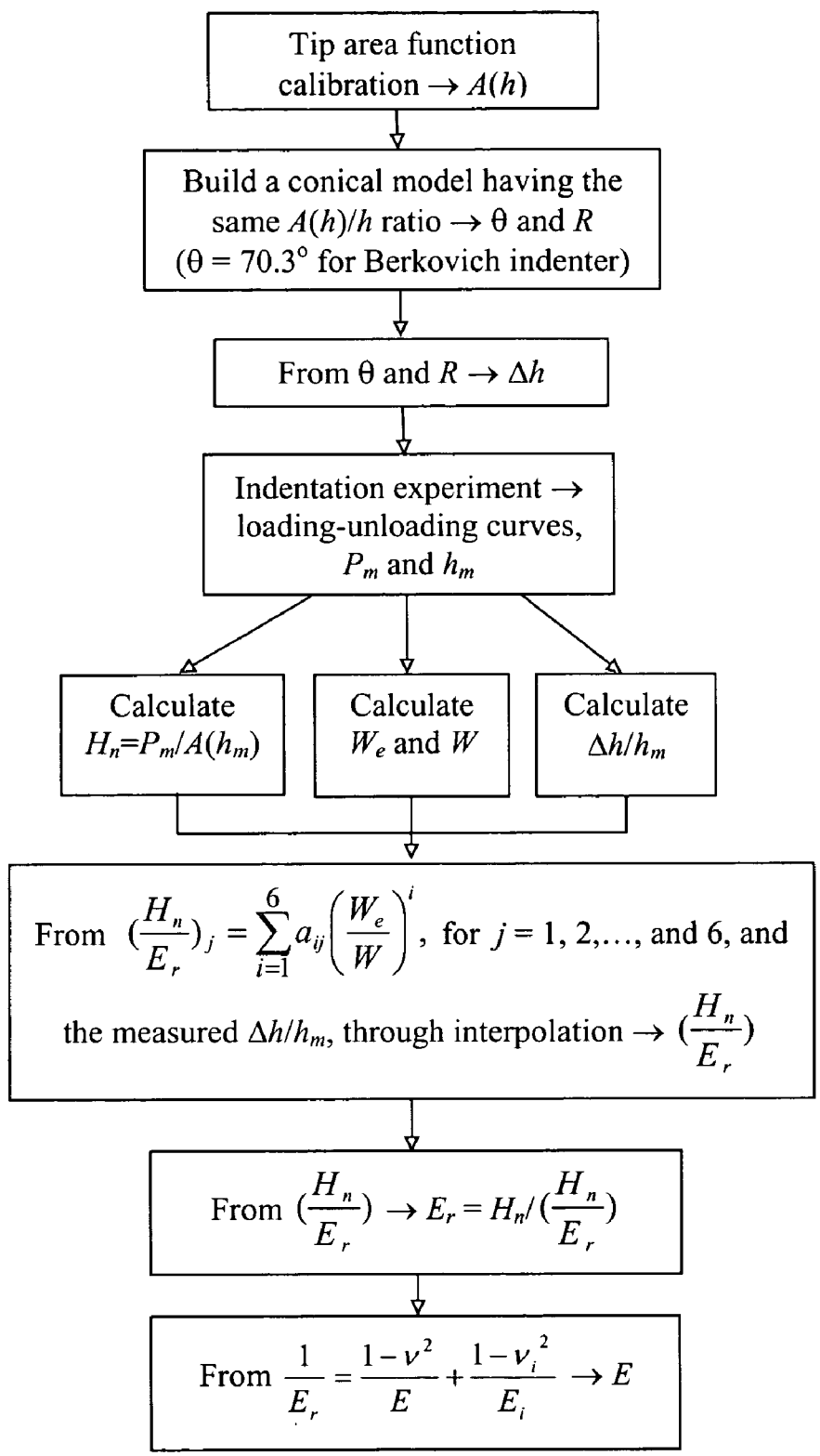
FIG. 7 shows a flow chart summarizing the procedures to derive the elastic modulus of an indented material.

FIG. 7 shows a flow chart summarizing the steps involved in the above analysis reaching the method of this invention.

EXAMPLES

Experimental Verification of the Method

The validity of the method was examined through indentation tests made on five materials, i.e. S45C carbon steel, 6061 aluminum alloy, tungsten single crystal, aluminum single crystal and fused silica. The surfaces of these samples were polished to mirror finish. A Nanoindenter IIs (Nano instruments inc.) equipped with a diamond Berkovich indenter with certain bluntness was used to perform the experiments. The real tip area function was calibrated first. The Berkovich indenter used in this exemplary demonstration is modeled with a conical indenter shape with a half-included angle $\theta$ of 70.3 degree and a spherical cap with a radius of R=650 nm. To show the equivalency between the real indenter tip and the non-ideal conical model, the calibrated area function A(h) of the former is converted into a radius function $r(h)=[A(h)/\pi]^{0.5}$, which is in good agreement with the radius of the conical model at all depth h. The absolute bluntness is thus calculated to be $\Delta h=(1/\sin\theta-1)R=40.4$ nm.

Figure 8:
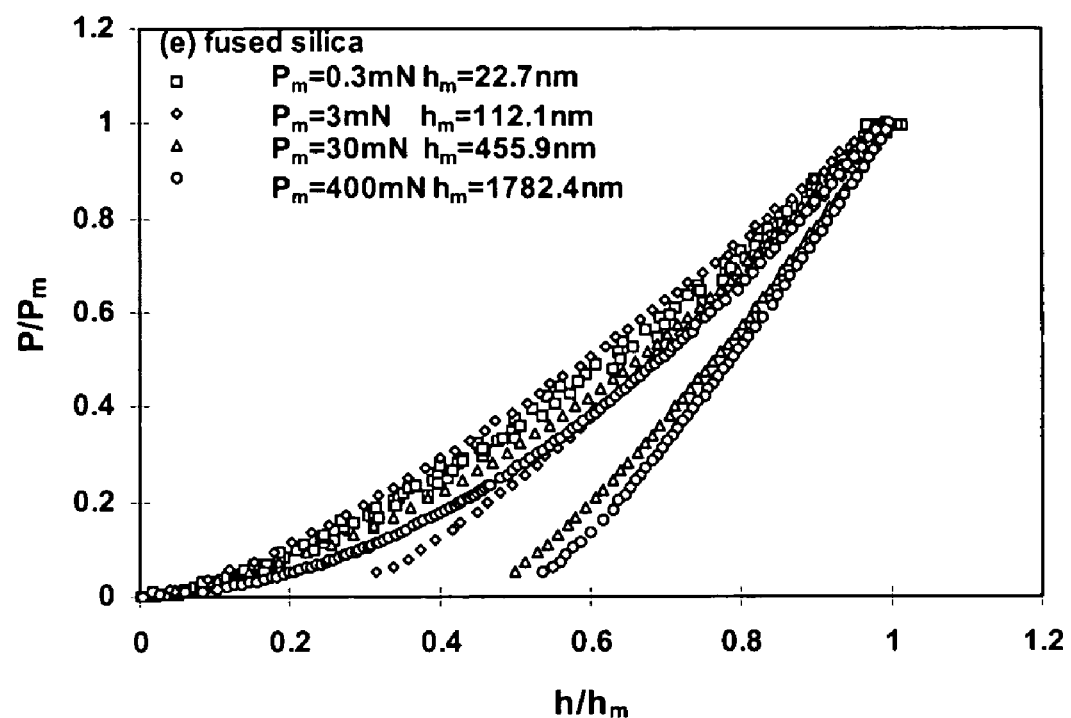
FIG. 8 shows the normalized load-unload curves corresponding to four load levels for (a) S45C carbon steel, (b) 6061 aluminum alloy, (c) tungsten single crystal, (d) aluminum single crystal and (e) fused silica.
Figure 9:
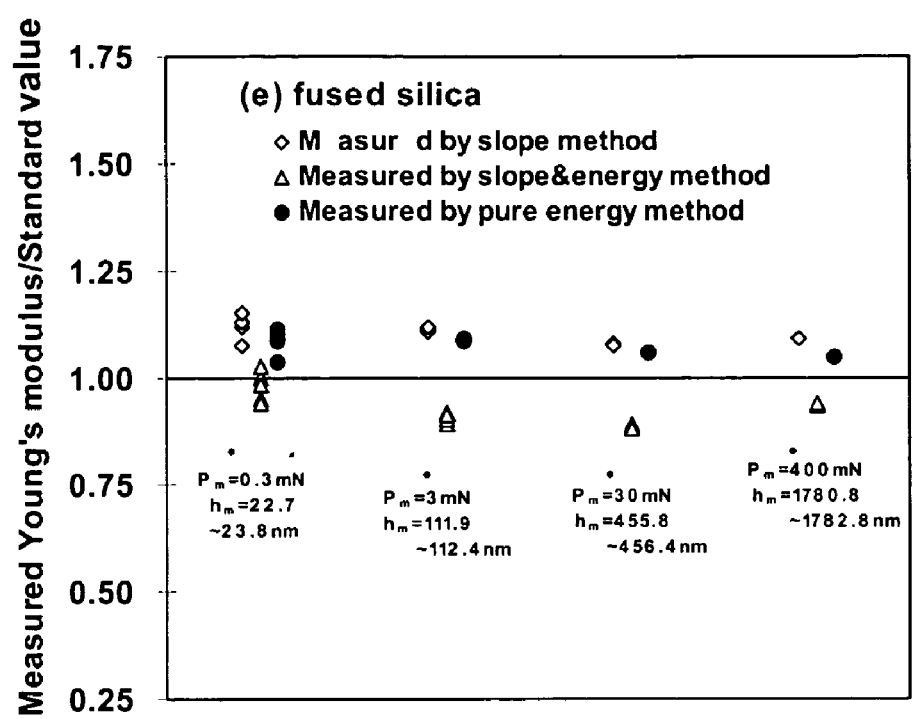
FIG. 9 shows the values of the normalized elastic modulus of (a) S45C carbon steel, (b) 6061 aluminum alloy, (c) tungsten single crystal, (d) aluminum single crystal and (e) fused silica with respect to the standard reference values of the corresponding bulk materials, as derived from the presently invented pure energy method, slope method and slope&energy method respectively.

Indentation tests were carried out on the samples with the maximum loads varying in the ranges of 0.3~400 mN for the S45C carbon steel, 0.1~400 mN for 6061 aluminum alloy, 0.5~400 mN for single crystal tungsten, 0.06~200 mN for aluminum single crystal, and 0.3~400 mN for fused silica. An experiment was designed to consist of segments of approaching, loading, holding, unloading and thermal drift correction. For each set of indentation parameters, measurements were repeated five times at different points on a sample surface. Typical load-unload curves corresponding to four load levels for each material are shown in FIG. 8 (a)–(e). They are obtained after the load frame stiffness correction and thermal drift correction. Applying the proposed method in this study and assuming that the elastic constants of the diamond indenter were $E_i$=1141 GPa and $v_i$=0.07, and the Poisson's ratios v of the indented materials were 0.3 for S45C carbon steel and 6061 aluminum alloy, 0.28 for tungsten single crystal, 0.347 for the aluminum single crystal, and 0.17 for the fused silica, the elastic modulus of the tested materials were conveniently determined. The data of elastic modulus were normalized with respect to the reference values of the corresponding bulk materials. The reference elastic modulus of the bulk carbon steel and aluminum alloy were obtained by performing standard uniaxial tensile tests. The specimens for the tensile tests were cut from the same ingots of the materials used for the indentation tests. The reference values of the tungsten single crystal, aluminum single crystal and fused silica are cited from the literature. These reference values of S45C carbon steel, 6061 aluminum alloy, tungsten single crystal, aluminum single crystal and fused silica are 200, 70.5, 409.8, 70.4 and 72 GPa, respectively. The indentation depth dependence of the normalized elastic modulus of the materials is shown in FIGS. 9 (a)–(e). Two groups of data attained by applying the slope method and slope&energy method are also generated and plotted in the figures for comparison. Data of the first group are from equation (1) with $\beta$=1.034. Data of the second group are not directly derived according to the formulas published in the papers reporting the slope&energy method, because in these papers, an ideally sharp indenter is used. However, based on spirit of the slope&energy method, the indenter bluntness effects can still be introduced through some modifications. By setting $\Delta h/h_m$, to be equal to 0, 0.5, 1.0, 1.5, 3.0 and 12.4336 successively, a set of six relationships between $H/E_r$ and $W_e/W$ are established based on the numerical simulations of indentation processes, which are expressed in the forms of polynomials:

$$\left(\frac{H}{E_r}\right)_j = \sum_{i=1}^{6} b_{ij} \left(\frac{W_e}{W}\right)^i \quad (12)$$

where j=1, 2, . . . , and 6 is used to index the six different relative bluntness values. The $b_{ij}$ coefficients in function (12) are derived and listed in Table II. With the use of the functions (12), a set of estimates of $H/E_r$ corresponding to the above six $\Delta h/h_m$ settings is obtained. The value of $H/E_r$=f($W_e/W$) corresponding to the measured $\Delta h/h_m$, value is determined through interpolation. $E_r$ is then derived from equation (3) with the f($W_e/W$) value as determined, maximum load $P_m$, $S_u$ and $\beta$=1.096 (M. Dao et al., Acta Mater. 49, 3899(2001)). It is seen immediately from FIGS. 9 (a)–(e) that the presently invented method gives better estimates to the elastic modulus for all of the materials measured at all depths. In contrast, the results obtained by using the slope or slope&energy methods exhibit relatively larger errors. It is conjectured that the precision of the initial unloading slope measurement and the principles underlying the slope and slope&energy models should be responsible to the deviations of the results from the real material properties.

While the preferred embodiment of the present invention has been described in detail by the examples, it is apparent that modifications and adaptations of the present invention will occur to those skilled in the art. Furthermore, the embodiments of the present invention shall not be interpreted to be restricted by the examples or figures only. It is to be expressly understood, however, that such modifications and adaptations are within the scope of the present invention, as set forth in the following claims. For instance, features illustrated or described as part of one embodiment can be used on another embodiment to yield a still further embodiment. Thus, it is intended that the present invention cover such modifications and variations as come within the scope of the claims and their equivalents.

List 1

| Symbol | Description |
|---|---|
| FEA | Finite element analysis |
| $\sigma$ | True stress of the indented material |
| $\epsilon$ | True strain of the indented material |
| $\sigma_y$ | Yield stress of the indented material |
| $\epsilon_y$ | Yield strain of the indented material, equal to $\sigma_y/E$ |
| n | Strain hardening exponent of the indented material |
| E | Elastic or Young's modulus of indented material |
| v | Poisson's ratio of indented material |
| $E_i$ | Elastic or Young's modulus of indenter |
| $v_i$ | Poisson's ratio of indenter |
| $E_r$ | Reduced elastic modulus of indented material, relating to E, v, $E_i$ and $v_i$ by: $\frac{1}{E_r} = \frac{1-v^2}{E} + \frac{1-v_i^2}{E_i}$ |
| $\beta$ | Indenter shape dependent constant |
| $P_m$ | Maximum indentation load |
| h | Indentation depth |
| $h_m$ | Maximum indentation depth, as shown in FIG. 1 |
| $h_c$ | Contact depth, as shown in FIG. 1 |
| $\Delta h$ | Absolute bluntness of the indenter, as shown in FIG. 4 |
| R | Radius of curvature of the cap of the conical indenter model, as shown in FIG. 4 |
| $r_b$ | Relative bluntness, defined as $\Delta h/h_m$ |
| A(h) | Cross sectional area of the indenter at depth h |
| A($h_m$) | Cross sectional area of the indenter at maximum indentation depth $h_m$, i.e. the maximum displacement of the indenter measured from the original sample surface |
| A($h_c$) | Cross sectional area of the indenter at the contact depth $h_c$ |
| r | Radius function defined as the radius of the conical indenter model $r = [A(h)/\pi]^{0.5}$ |
| $W_e$ | Elastic work done by the indenter in an unloading process |
| W | Total work done by the indenter in a loading process |
| H | Hardness, H = $P_m/A(h_c)$ |
| $H_n$ | Nominal hardness, $H_n = P_m/A(h_m)$ |
| $c_i$ | i = 1, 2, . . ., and 8<br>Coefficients describing the area function of a Berkovich indenter. |
| $a_{ij}$ | i = 1, 2, . . ., and 6;<br>j = 1, 2, . . ., and 6<br>Coefficients in the polynomial for describing the function-like relationship between $H_n/E_r$ and $W_e/W$, as expressed in function (11) |
| $b_{ij}$ | i = 1, 2, . . ., and 6;<br>j = 1, 2, . . ., and 6<br>Coefficients in the polynomial for describing the function-like relationship between $H/E_r$ and $W_e/W$, as expressed in function (12) |

TABLE I

| j | $(\Delta h/h_m)_j$ | $a_{1j}$ | $a_{2j}$ | $a_{3j}$ | $a_{4j}$ | $a_{5j}$ | $a_{6j}$ |
|---|---|---|---|---|---|---|---|
| 1 | 0 | 0.18408 | −0.24835 | 0.50721 | −0.86118 | 0.75187 | −0.25388 |
| 2 | 0.5 | 0.16352 | −0.26383 | 0.65713 | −1.13560 | 0.96922 | −0.31700 |
| 3 | 1.0 | 0.12903 | −0.21498 | 0.54428 | −0.91821 | 0.76181 | −0.24346 |
| 4 | 1.5 | 0.10377 | −0.16829 | 0.39042 | −0.60740 | 0.47293 | −0.14430 |
| 5 | 3.0 | 0.07009 | −0.10262 | 0.22412 | −0.34838 | 0.27553 | −0.08609 |
| 6 | 12.4336 | 0.03560 | −0.06993 | 0.19772 | −0.34292 | 0.28861 | −0.09316 |

TABLE II

| j | $(\Delta h/h_m)_j$ | $b_{1j}$ | $b_{2j}$ | $b_{3j}$ | $b_{4j}$ | $b_{5j}$ | $b_{6j}$ |
|---|---|---|---|---|---|---|---|
| 1 | 0 | 0.14736 | 0.15960 | −0.23052 | 0.12656 | 0.18514 | −0.19733 |
| 2 | 0.5 | 0.11886 | 0.28747 | −1.02269 | 1.92793 | −1.69970 | 0.55020 |
| 3 | 1.0 | 0.10564 | 0.05871 | −0.13130 | 0.09605 | 0.06585 | −0.08460 |
| 4 | 1.5 | 0.09346 | −0.07342 | 0.47969 | −1.13309 | 1.16492 | −0.44249 |
| 5 | 3.0 | 0.05628 | 0.07060 | −0.25815 | 0.45620 | −0.37043 | 0.10768 |
| 6 | 12.4336 | 0.02867 | 0.00698 | 0.01887 | −0.10942 | 0.15827 | −0.07416 |

The invention claimed is:

1. A method of understanding the mechanical properties of a material comprising:

determining the elastic modulus of a material having a Poisson's ratio v by a Berkovich indenter having an elastic modulus $E_i$, a Poisson's ratio $v_i$, and a cross sectional area A(h) as a function of depth h, including the following steps a) to h):

a) modeling the Berkovich indenter with a conical shape with a spherical cap providing a blunt tip which is assigned to have a half-included θ, and a radius R of the cap or an absolute bluntness value Δh to ensure that its cross sectional area is the same as that of the real indenter for all h values;

b) measuring maximum load $P_m$, maximum indentation depth $h_m$, elastic work $W_e$ and total work W;

c) calculating nominal hardness $H_n$, where;

$$H_n = \frac{P_m}{A(h_m)};$$

d) calculating a set of estimates of $$\frac{H_n}{E_r}$$

from a set of relationships between $$\frac{H_n}{E_r} \text{ and } \frac{W_e}{W}$$

derived from numerical simulations of indention processes corresponding to different settings of relative bluntness defined as $\Delta h/h_m$, wherein;

$$\frac{1}{E_r} = \frac{1-v^2}{E} + \frac{1-v_i^2}{E_i};$$

e) determining $$\frac{H_n}{E_r}$$

corresponding to the experimentally measured $\Delta h/h_m$ value through interpolation;

f) calculating a reduced elastic modulus $E_r$ of the material by dividing $H_n$ with the estimate $$\frac{H_n}{E_r}$$

value;

g) calculating the material elastic modulus E from;

$$E = \frac{1-v^2}{\frac{1}{E_r} - \frac{1-v_i^2}{E_i}}.$$

h) utilizing the calculated elastic modulus E to understand the mechanical properties of a material.

2. The method of claim 1, wherein the relationship between $$\frac{H_n}{E_r} \text{ and } \frac{W_e}{W} \text{ is } \left(\frac{H_n}{E_r}\right)_j = \sum_{i=1}^{6} a_{ij}\left(\frac{W_e}{W}\right)^i,$$

where the values of the coefficients $a_{ij}$ depend on the area function A(h) of the indenter at large h beyond the blunt region.

3. The method of claim 2, wherein i=1, 2, . . ., and 6 for indexing the six terms in a relationship between $$\frac{H_n}{E_r} \text{ and } \frac{W_e}{W}.$$

4. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 3.

5. The method of claim 2, wherein j=1, 2, . . . , and 6 corresponding to six $$\frac{H_n}{E_r} - \frac{W_e}{W}$$

relationships corresponding to six different settings of relative bluntness $\Delta h/h_m$.

6. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 4.

7. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 2.

8. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 1.

9. A method of understanding the mechanical properties of a material comprising:
   determining an elastic modulus of a material upon indentation by a blunted Berkovich indenter with a rounded, spherical cap providing a blunt tip on an indenter contact area including the steps of:
   a) measuring maximum load, the indentation depth, elastic work and total work;
   b) determining a nominal hardness value calculated from the measured maximum load and indentation depth;
   c) utilizing a set of material independent correlations between the ratio of nominal hardness to reduced modulus, and the ratio of elastic work to total work to calculate said elastic modulus E from $$E = \frac{1 - v^2}{\frac{1}{E_r} - \frac{1 - v_i^2}{E_i}};$$

d) utilizing the calculated elastic modulus E to understand the mechanical properties of a material.

10. A method of understanding the mechanical properties of a material comprising:
   determining the elastic modulus of a material having a Poisson's ratio v by a Berkovich indenter having an elastic modulus $E_i$, a Poisson's ratio $v_i$, and a cross sectional area A(h) as a function of depth h, including the following steps a) to h):
   a) modeling the Berkovich indenter with a conical shape with a spherical cap which is assigned to have a half-included θ, and a radius R of the cap and an absolute bluntness value Δh to ensure that its cross sectional area is the same as that of the real indenter for all h values;
   b) measuring maximum load $P_m$, maximum indentation depth $h_m$, elastic work $W_e$ and total work W;
   c) calculating nominal hardness $H_n$, where;

$$H_n = \frac{P_m}{A(h_m)};$$

d) calculating a set of estimates of $$\frac{H_n}{E_r}$$

from a set of relationships between $$\frac{H_n}{E_r}$$

and $W_e/W$ derived from numerical simulations of indention processes corresponding to different settings of relative bluntness defined as $\Delta h/h_m$, wherein;

$$\frac{1}{E_r} = \frac{1 - v^2}{E} + \frac{1 - v_i^2}{E_i};$$

e) determining $$\frac{H_n}{E_r}$$

corresponding to the experimentally measured $\Delta h/h_m$ value through interpolation;
   f) calculating a reduced elastic modulus $E_r$ of the material by dividing $H_n$ with the estimate $$\frac{H_n}{E_r}$$

value;
   g) calculating the material elastic modulus E from $$E = \frac{1 - v^2}{\frac{1}{E_r} - \frac{1 - v_i^2}{E_i}},$$

wherein Δh measures the depth change between an end point of the conical shape if the indenter continued to the end point and an end point of the spherical cap, and wherein Δh>0;

h) utilizing the calculated elastic modulus E to understand the mechanical properties of a material.

11. The method of claim 10, wherein the relationship between $$\frac{H_n}{E_r} \text{ and } \frac{W_e}{W} \text{ is } \left(\frac{H_n}{E_r}\right)_j = \sum_{i=1}^{6} a_{ij}\left(\frac{W_e}{W}\right)^i,$$

where the values of the coefficients $a_{ij}$ depend on the area function A(h) of the indenter at large h beyond the blunt region.

12. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 10.

13. A method of understanding the mechanical properties of a material comprising:

determining the elastic modulus of a material having a Poisson's ratio v by a Berkovich indenter having an elastic modulus $E_i$, a Poisson's ratio $v_i$, and a cross sectional area A(h) as a function of depth h, including the following steps a) to h):

a) modeling the Berkovich indenter with a conical shape with a spherical cap which is assigned to have a half-included θ, and a radius R of the cap or an absolute bluntness value Δh to ensure that its cross sectional area is the same as that of the real indenter for all h values;

b) measuring maximum load $P_m$, maximum indentation depth $h_m$, elastic work $W_e$ and total work W;

c) calculating nominal hardness $H_n$, where;

$$H_n = \frac{P_m}{A(h_m)};$$

d) calculating a set of estimates of $$\frac{H_n}{E_r}$$

from a set of relationships between $$\frac{H_n}{E_r}$$

and $$\frac{W_e}{W}$$

derived from numerical simulations of indention processes corresponding to different settings of relative bluntness defined as $\Delta h/h_m$, wherein;

$$\frac{1}{E_r} = \frac{1-v^2}{E} + \frac{1-v_i^2}{E_i};$$

e) determining $$\frac{H_n}{E_r}$$

corresponding to the experimentally measured $\Delta h/h_m$ value through interpolation;

f) calculating a reduced elastic modulus $E_r$ of the material by dividing $H_n$ with the estimate $$\frac{H_n}{E_r}$$

value;

g) calculating the material elastic modulus E from $$E = \frac{1-v^2}{\frac{1}{E_r} - \frac{1-v_i^2}{E_i}},$$

wherein the relationship between $$\frac{H_n}{E_r} \text{ and } \frac{W_e}{W} \text{ is } \left(\frac{H_n}{E_r}\right)_j = \sum_{i=1}^{6} a_{ij}\left(\frac{W_e}{W}\right)^i,$$

where the values of the coefficients $a_{ij}$ depend on the area function A(h) of the indenter at large h beyond the blunt region;

h) utilizing the calculated elastic modulus E to understand the mechanical properties of a material.

14. The method of claim 13, wherein i=1, 2, . . ., and 6 for indexing the six terms in a relationship between $$\frac{H_n}{E_r} \text{ and } \frac{W_e}{W}.$$

15. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 14.

16. The method of claim 13, wherein j=1, 2, . . ., and 6 corresponding to six $$\frac{H_n}{E_r} - \frac{W_e}{W}$$

relationships corresponding to six different settings of relative bluntness $\Delta h/h_m$.

17. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 15.

18. An apparatus for determining an elastic modulus E of a material having a Poisson's ratio v by using a Berkovich indenter having an elastic modulus $E_i$, a Poisson's ratio $v_i$, and a cross sectional area A(h) as a function of depth h, where the indenter is modeled with a conical shape having a half-included angle and a spherical cap such that its cross sectional area is equal to A(h) at all h values, including a processor incorporating the method of claim 13.

* * * * *